(12) United States Patent
Bozukova et al.

(10) Patent No.: US 11,337,796 B2
(45) Date of Patent: May 24, 2022

(54) INTRAOCULAR LENS

(71) Applicant: PHYSIOL, Liège (BE)

(72) Inventors: Dimitriya Bozukova, Grivegnee (BE); Christophe Pagnoulle, Verviers (BE); Saud Redzovic, Liège (BE)

(73) Assignee: PHYSIOL, Liège (BE)

( * ) Notice: Subject to any disclaimer, the term of this patent is extended or adjusted under 35 U.S.C. 154(b) by 0 days.

(21) Appl. No.: 15/762,702

(22) PCT Filed: Sep. 13, 2016

(86) PCT No.: PCT/EP2016/071485
§ 371 (c)(1),
(2) Date: Mar. 23, 2018

(87) PCT Pub. No.: WO2017/050607
PCT Pub. Date: Mar. 30, 2017

(65) Prior Publication Data
US 2018/0263761 A1  Sep. 20, 2018

(30) Foreign Application Priority Data
Sep. 23, 2015  (BE) .................. 2015/5589

(51) Int. Cl.
*A61F 2/16* (2006.01)
(52) U.S. Cl.
CPC .......... *A61F 2/1648* (2013.01); *A61F 2/1613* (2013.01); *A61F 2/1618* (2013.01); *A61F 2/1654* (2013.01); *A61F 2002/1681* (2013.01); *A61F 2210/00* (2013.01); *A61F 2220/00* (2013.01); *A61F 2220/005* (2013.01)

(58) Field of Classification Search
CPC .................................................... A61F 2/1648
See application file for complete search history.

(56) References Cited

U.S. PATENT DOCUMENTS 4,734,095 A * 3/1988 Siepser ................ A61F 2/1613
  623/6.43
5,117,306 A * 5/1992 Cohen .................. G02B 5/1876
  351/159.11

(Continued)

FOREIGN PATENT DOCUMENTS

WO  2005000551 A2  1/2005
WO  2006063994 A1  6/2006

(Continued)

OTHER PUBLICATIONS

International Search Report in corresponding International Application No. PCT/EP2016/071485, dated Jan. 30, 2017, 7 pages.

*Primary Examiner* — Leslie Lopez
(74) *Attorney, Agent, or Firm* — Fitch, Even, Tabin & Flannery LLP

(57) ABSTRACT

The present invention relates to an intraocular lens comprising:
a primary lens (1000) having a first focal length, a first surface, and a second surface;
a secondary lens (2000) having at least two focal lengths, a first surface (2100), and a second surface (2200), wherein the second surface (2200) of the secondary lens (2000) conforms to the first surface of the primary lens (1000), while the secondary lens (2000) is attached to the primary lens (1000) by peelable adhesive forces over substantially its second surface (2200).

20 Claims, 4 Drawing Sheets

(56) References Cited

U.S. PATENT DOCUMENTS

| | | | |
|---|---|---|---|
| 5,133,747 A | 7/1992 | Feaster | |
| 5,135,592 A * | 8/1992 | Melvin | B29C 66/1162 |
| | | | 156/73.1 |
| 5,152,788 A | 10/1992 | Isaacson et al. | |
| 6,113,633 A | 9/2000 | Portney | |
| 2004/0252274 A1* | 12/2004 | Morris | G02C 7/042 |
| | | | 351/159.44 |
| 2014/0268027 A1* | 9/2014 | Pugh | G02C 7/083 |
| | | | 351/159.33 |

FOREIGN PATENT DOCUMENTS

| | | |
|---|---|---|
| WO | 2011065986 A1 | 6/2011 |
| WO | 2011092169 A1 | 8/2011 |
| WO | 2014197170 A1 | 12/2014 |

* cited by examiner

INTRAOCULAR LENS

OBJECT OF THE INVENTION

The present invention relates to an intraocular lens comprising a removable optical part.

PRIOR ART

Due to the aging of the population, cataract operations are becoming more and more frequent. In this operation, an intraocular lens (IOL) is implanted in place of the opacified lens. In addition, as life expectancy in good health increases, the duration of use of these IOLs becomes longer and longer. In addition, today we are trying to constantly improve the quality of implants and their comfort of use.

A recent major improvement in this field has been the use of high performance multifocal implants as described for example in WO 2011/092169. In this type of lens, the light intensity reaching the lens is distributed along several focal lengths: for example, in 3 focal lengths, the first allowing near vision, the second allowing vision at an intermediate distance, and the third for long distance viewing.

The advantage of this type of device is to obtain satisfactory visual comfort at any distance without the use of additional corrective glasses. Multifocal lenses are often implanted in relatively young patients with presbyopia who have a healthy retina.

Multifocal lenses are intrinsically associated with a lower contrast resulting from the distribution of energy between two or more focal points.

During natural aging and/or a possible occurrence of a disease, for example age-related macular degeneration (AMD), the retina gradually loses its sensitivity, so that the intensity distributed to each focal point becomes insufficient for comfortable vision.

On the other hand, multifocal lenses are associated with the risk of non-optimal vision because of the superimposition of images from the first, second and, possibly, third focal lengths. Despite the fact that most patients become accustomed to their psychoplasticity, others do not even long after surgery. In other cases, posterior segment surgery in patients implanted with multifocal lenses may be difficult due to image distortion of the retina through the lens.

In the aforementioned cases, it becomes necessary to return to a monofocal correction for distance vision, and correction of the view by corrective glasses for other distances.

The use of traditional multifocal lenses then requires the removal of the entire implant, which causes significant trauma because of the fusion of the capsules.

The patent application WO 2011/065986 describes an adjustable multifocal lens comprising a multifocal base lens and a secondary multifocal lens having negative optical power. When these two lenses are combined, they jointly produce a monofocal lens. This makes it possible to find the optimum contrast normally obtained for a monofocal lens. Nevertheless, this method has the disadvantage that it is extremely difficult to correctly align the two optics in an intraocular intervention, which leads to additional optical aberrations. In addition, during placement of the secondary lens, a protein biofilm has generally already formed on the surface of the initial lens, causing further degradation of the optical quality of the assembly.

Patent application WO 2005/000551 discloses an adjustable intraocular lens comprising a primary lens and a secondary lens. These lenses are intended to be assembled in the patient's eye by successive insertion and in vivo positioning during one or more operations, with all the disadvantages associated with these multiple interventions. Again, the in vivo assembly represents a risk of misalignment, while the presence of biological fluids between the two lenses during assembly also presents a risk of occurrence of optical defects.

Patent application WO 2014/197170 describes intraocular lenses in two parts, wherein the parts are assembled in the eye to adapt the optical characteristics of the implant after the operation. These different parts are assembled by means of mechanical fasteners.

OBJECT OF THE INVENTION

The present invention aims to provide a multifocal intraocular lens that may be subsequently modified to a monofocal intraocular lens in a less traumatic method than the complete replacement of the lens.

Furthermore, the use of the device seeks to limit the risks associated with multiple insertions involved in an assembly in the eye and/or explantation of an entire intraocular lens. These risks are mainly related to bacterial contamination, residual astigmatism, rupture of the capsular bag, all of which are traumatic for the patient.

SUMMARY OF THE INVENTION

The present invention relates to an intraocular lens comprising:
- a primary lens having a first focal length, a first surface, and a second surface;
- a secondary lens having at least two focal lengths, a first surface and a second surface, wherein the second surface of the secondary lens conforms to the first surface of the primary lens, while the secondary lens is fixed to the primary lens by peelable adhesive forces on the essential part of its second surface.

Advantageously, the primary lens is a refractive lens, wherein the refractive lens preferably allows a clear view at long distance.

Preferably, the primary lens or the secondary lens comprises a surface, toric or not, with compensation for spherical corneal abberrations.

Advantageously, the secondary lens is adapted to be covered by the rhexis of the capsular bag, allowing the explantation of the secondary lens in the event of a problem within 6 months of its implantation, i.e. before the complete fusion of the posterior and anterior parts of the capsular bag.

It may also be advantageous in some cases if the secondary lens is not covered by the rhexis of the capsular bag, which would allow explantation of the secondary lens in the event of problems at any time after implantation.

Preferably, the secondary lens is a diffractive lens having an order x having an infinite focal length, and at least an order x+1 having a finite focal length. This diffractive lens is preferably in the form of a thin meniscus having a central thickness less than 500 µm, preferably less than 200 µm.

Advantageously, the combination of the primary lens and the secondary lens forms a multifocal lens whose optical characteristics make it possible to obtain a sharp image at great distance superimposed on a sharp image at short distance. Preferably, an additional focal distance makes it possible to obtain a net image at intermediate distance.

Advantageously, the materials forming the lenses have sufficient intrinsic adhesion to maintain the integrity of the lens in an aqueous medium and during implantation.

Preferably, the materials forming the primary lens and the secondary lens comprise at least one copolymer, wherein the copolymer comprised in the primary lens comprises a monomer common with the copolymer comprised in the secondary lens. This common monomer makes it possible to modulate the intrinsic adhesion between the two lenses, wherein the closer are the compositions of the two polymers, the higher is the adhesion.

The common monomer is preferably an acrylate, advantageously chosen from the group consisting of 2-hydroxyethylmethylacrylate, methylmethacrylate, ethylmethylacrylate, hydroxyhexylmethacrylate, ethoxyethylmethacrylate, 2-phenylethylacrylate, ethylacrylate; 2-phenylethylmethacrylate, 2,2,2-trifluoroethylmethacrylate, ethylene-glycolphenyletheracrylate, butylacrylate, dimethyldiphenylsiloxane and dimethylsiloxane.

The materials used for both the primary lens and the secondary lens preferably form a hydrogel in an aqueous medium.

The secondary lens preferably comprises centering means of the secondary lens on the primary lens.

CAPTIONS OF THE FIGURES

1000: primary lens
2000: secondary lens
1100, 1110, 1120, 1130: optical portion of the primary lens
1200: haptic double c-loop
1210: closed quadrupole haptic
1220: haptic C-loop
1230: flat haptic
1300, 1310, 1320, 1330: junction between optical and haptic parts
2100: first optical surface of the secondary lens
2200: second optical surface of the secondary lens
2300: centering means

DETAILED DESCRIPTION OF THE INVENTION

The present invention relates to a multifocal system of intraocular lenses comprising a conventional monofocal primary lens and a removable multifocal secondary lens. The primary and secondary lenses are assembled prior to their storage and sterilized packaging via peelable adhesive forces. By "peelable" is meant here an adhesion allowing peeling of the lenses by adhesive rupture.

In the case of adhesion obtained by means of an adhesive (glue), the latter is to be chosen so that the adhesive has a higher affinity on the surface of the removable multifocal lens compared with its affinity to the monofocal lens, with or without correction of corneal astigmatism. In this way, during the removal of the multifocal lens, the adhesive remains on it, thus avoiding degrading the optical characteristics of the monofocal lens.

Nevertheless, it is always difficult to ensure that all the adhesive remains on the removable lens. In order to avoid this risk, the adhesion between the two lenses is advantageously obtained by an intrinsically reversible interfacial interaction with the chemical compositions of their constituent materials.

Advantageously, the multi-component intraocular lens of the invention may be implanted in the eye in a single insertion step, allowing the transformation of the multifocality into monofocality at any time following surgery by a simple withdrawal of the multifocal element through a very small incision that is less traumatic than the complete replacement of a traditional multifocal lens.

Figure 1:
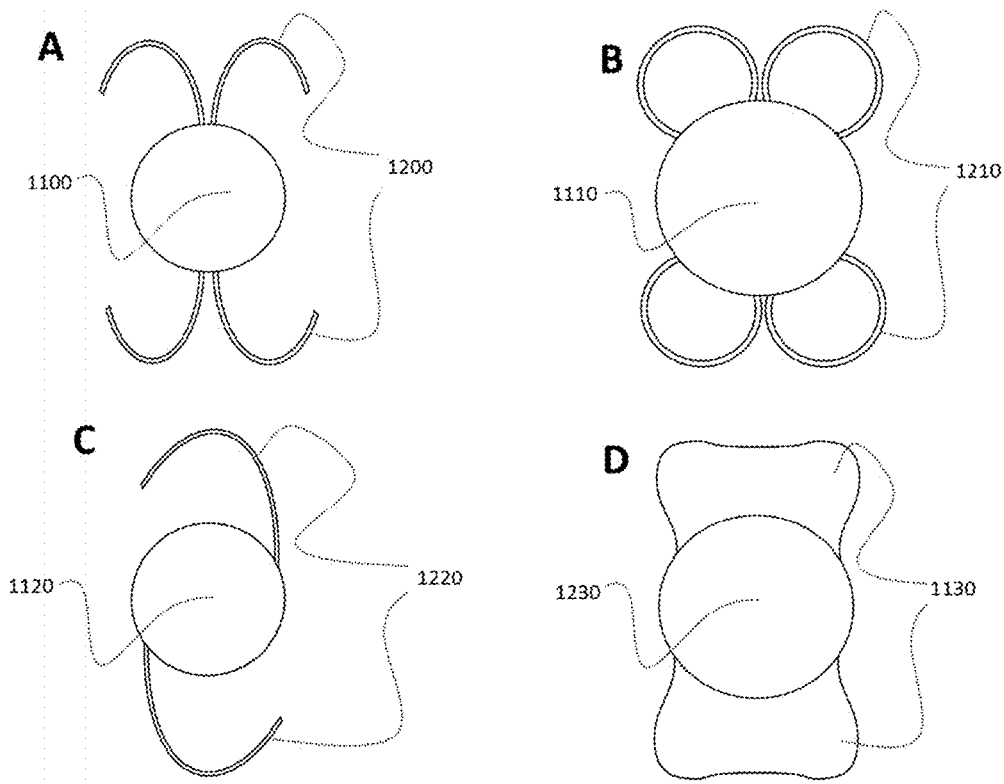
FIG. 1 represents conventional lenses that may receive a secondary lens to form an intraocular implant according to the invention.
Figure 2:
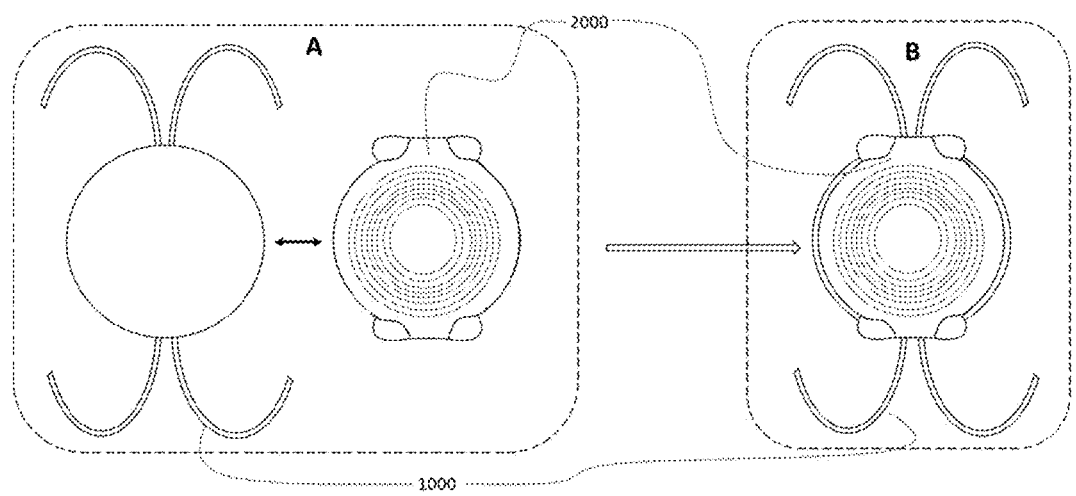
FIG. 2 represents an example of a lens according to the invention before (2-A) and after assembly (2-B).

Preferably, the primary lens is a conventional lens allowing viewing from a distance. It may furthermore comprise or not an aspheric, toric or chromatic component to compensate for this type of aberration, depending on the patient in question. It may be a lens intended for implantation in the capsular bag, in the sulcus or in the anterior chamber of the eye. Examples of conventional primary lens models are shown in FIG. 1. They may be, for example, double-C-Loop (FIG. 1A), closed quadrupode (FIG. 1B), C-loop (FIG. 1C) or flat haptic (FIG. 1D).

The primary lens 1000 has an optical portion 1100, 1110, 1120, 1130 and a haptic portion 1200, 1210, 1220, 1230, wherein the optical portion is connected to the haptic portion via an optical/haptic junction 1300, 1310, 1320, 1330.

The secondary lens comprises a first optical surface 2100 having a multifocal optical diffractive or refractive component. This surface is preferably the free surface of this secondary lens 2100 (i.e. it is the surface that is not in contact with the primary lens).

The secondary lens has a second optical surface 2200 in contact with the primary lens. This surface preferably has monofocal refractive characteristics.

Advantageously, the secondary lens has centering means 2300 of the secondary lens on the primary lens. These centering means preferably allow centering of the secondary lens on the primary lens with a tolerance of less than 0.15 mm, preferably less than 0.1 mm, ideally less than 0.05 mm. For example, the secondary lens may comprise positioning means relying on the haptic portions of the primary lens (i.e. the parts for positioning the primary lens in the eye 1200, 1210, 1220, 1230). More preferably, the secondary lens comprises positioning means bearing on the haptic parts of the primary lens, as well as on the junction 1300, 1310, 1320, 1330 between the latter and the optical part.

The advantage of this two-part type of lens is that, in the event of a reduction of the sensitivity of the retina, it is possible, with a minimally invasive operation, to remove the secondary lens, and thus to reconcentrate all of the light intensity on a single optical path, usually the optical path for long-range viewing.

Advantageously, the primary lens is a refractive lens, preferably allowing the formation of a sharp image on the retina of objects located at a great distance (more than 2 m, focusing of objects "at infinity").

Preferably, the secondary lens is a multifocal diffractive lens having a diffraction order x having an infinite focal length with a diopter of 0D and at least an order of x+1 having an intermediate or near focal length. In fact, the order x allows the image formed by the unchanged primary lens to be maintained, and to superimpose thereon an image formed by the order x+1.

Advantageously, the secondary lens is a multifocal diffractive lens having two diffraction profiles, wherein:
the first profile has a diffraction order x having an infinite focal length with a diopter of 0D and at least one order x+1 having an intermediate focal length,
wherein the second profile has a diffraction order y having an infinite focal length with a diopter of 0D and at least one order y+1 having a close focal length,
the energy dedicated to the order x+2 of the first profile is superimposed on the energy dedicated to the order y+1 of the second profile, and contributes positively to the transfer of the contrast. In fact, the order x of the first profile and the order y of the second profile then make it possible to maintain the image formed by the unchanged primary lens, and to superimpose thereon an image formed by the order x+1 and an image formed by the order y+1.

In these examples, the orders x and y may be greater than or equal to 0, with a diopter of 0D. This type of superimposition is, for example, described in documents WO 2011/092169 and European Patent Application No. 180802.6 which we incorporate here for reference.

The use of a diffractive secondary lens makes it possible to use a secondary lens in the form of a thin meniscus, preferably less than 500 μm in thickness, more preferably less than 200 μm, and even more preferably less than or equal to 100 μm. This thickness is measured at the center of the meniscus. This makes it possible to use as a primary lens a conventional intraocular implant to which a thin meniscus is added on which a particular multifocal texture, preferably diffractive, makes it possible to obtain additional focusing. The small thickness of the secondary lens then allows the injection process of the complete lens (primary+secondary) to be left unchanged compared to the injection of a conventional intraocular implant. The thinness of the secondary lens also allows effective folding allowing its removal by a small size incision.

Advantageously, the combination of the primary lens and the secondary lens forms a multifocal lens whose optical characteristics make it possible to obtain a sharp image on the retina of objects located at great distances superimposed on a sharp image of objects located at a short distance. Preferably, the secondary lens comprises an additional focal distance to obtain a sharp image of objects located at an intermediate distance.

Preferably, the two lenses are fixed without the use of an adhesive layer: in fact, the use of such layers poses many problems. On the one hand, these layers must have good biocompatibility for a final implantation in the eye, while, on the other hand, it is essential that during the process of removal of the secondary lens, there remains no trace of the adhesive that could degrade the optical quality of the primary lens. To this end, the materials forming the lens advantageously have sufficient intrinsic adhesion to maintain the integrity of the lens in an aqueous medium.

Advantageously, the secondary lens comprises a hydrogel as described in WO 2006/063994 that is incorporated here for reference. This hydrogel comprises at least one polymer formed by polymerization of at least one hydrophilic (meth) acrylic monomer such as 2-hydroxyethylmethacrylate (HEMA), at least one hydrophobic monomer, preferably with a high refractive index so that ethylene glycol phenyl ether acrylate (EGPEA), and at least one hydrophobic crosslinking agent such as poly (propylene glycol dimethacrylate) PPGDMA. It has been demonstrated that this type of composition allows adhesion on most conventional intraocular lens compositions, whether based on hydrophilic hydrogel compositions or on hydrophobic compositions, typically based on acrylate and methacrylate-based compositions.

A particularly advantageous composition is characterized in that the hydrophilic monomer and the hydrophobic monomer together represent at least 90% by weight of the overall composition, while the crosslinking agent is a hydrophobic polymer which has several polymerizable ethylenically unsaturated groups and comprises a number of base units (degree of polymerization) equal to or greater than 5.

Other hydrophilic monomers (i.e. monomers whose homopolymers are hydrophilic) may be selected from the group consisting of 2-hydroxyethylacrylate, 2-hydroxyethylmethacrylate (HEMA), acrylamide, N-ornithine acrylamide, N-(2)-hydroxypropyl) acrylamide, polyethylene glycol acrylates, polyethylene glycol methacrylates, N-vinyl pyrrolidone, N-phenylacrylamide, dimethylaminopropyl methacrylamide, acrylic acid, benzylmethacrylamide, 4-hydroxybutylmethaerylate, glycerol mono methaerylate, glycerol monoacrylate, 2-sulfoethylmethacrylate, phenoxyethyl acrylate, phenoxyethylmethacrylate, 2-(2-ethoxyethoxy) ethyl acrylate, 2-(2-thoxyethoxy) ethyl methacrylate, furfuryl acrylate, furfuryl methaerylate, and methyithioethylacrylamide and mixtures thereof.

Other suitable hydrophobic monomers (i.e. monomers whose homopolymers are hydrophobic) may be selected from the group consisting of ethylene glycol phenyl ether acrylate (EGPEA), lauryl methacrylate, lauryl acrylate, 2-ethylhexyl acrylate, 2-ethythexyl methacrylate, n-decyl acrylate, n-decyl methacrylate, hexyl acrylate, hexyl methamlate, stearyl acrylate, stearyl methacrylate, isodecyl acrylate, isodecyl methacrylate, isobornyl acrylate, isobornyl methacrylate, vinyl laurate, vinyl stearate, 1-hexadecyl acrylate, 1-hexadecyl methacrylate, n-myristyl acrylate, n-myristyl methacrylate, n-dodecyl methacrylamide, butyl acrylate, n-butyl methacrylate, isooctyl acrylate, isotridecyl acrylate, isooctyl methacrylate, and isotridecyl methacrylate, and mixtures thereof.

Preferably, the composition of the primary lens is characterized in that it contains 29 to 39% by weight of at least one first hydrophilic monomer and 53 to 63% by weight of at least one second hydrophobic monomer with a high index of refraction. "High refractive index" means an index greater than 1.42 at 589 nm.

Advantageously, the proportion between the hydrophilic monomer and the monomer with high refractive index is reversed in the composition of the secondary lens.

Even more advantageously, the sum of the concentrations by weight of the hydrophilic monomer in the materials of the primary lens and the secondary lens are comparable or equal to the sum of the concentrations by weight of the hydrophobic monomer with a high index of refraction in the materials of the primary lens and the secondary lens. This results in the chemical complementarity of the two materials and results in proper adhesion of one to the other.

When the secondary lens comprises a hydrogel, it is advantageously applied on the primary lens in an aqueous medium, wherein the secondary lens is in the partially hydrated state. The hydration method thus induces adequate adhesion of the secondary lens on the primary lens. The partially hydrated state not only makes it possible to obtain adhesion between the two lenses, but also makes it possible to regulate the level of this adhesion as well as to regulate the potential problems of differential expansion occurring during hydration: the more the dehydration of the secondary lens before the bonding is effected, the more the adhesion will be strong, but also, the more the expansion of the secondary lens is significant, this may cause internal tension problems inducing unwanted deformations.

Preferably, the secondary lens is partially dehydrated by surface drying of the secondary lens. The secondary lens is then immediately pressed onto the primary lens in an aqueous medium.

The secondary lens may preferably be of a diameter smaller than the optics of the primary lens, and advantageously of a diameter smaller than the rhexis, so that the secondary lens may be peeled without interfering with the edge of the rhexis adhering to the optics of the primary lens.

Example 1

In peeling experiments, two types of rupture may be observed: so-called adhesive ruptures wherein the separation occurs at the interface between the two assembled objects, or so-called cohesive ruptures wherein the rupture occurs in the volume of one of the two objects.

In the present case, it is important that the ruptures between the primary lens and the secondary lens are of the adhesive type, in order to keep the optical properties of the primary lens unchanged.

Two types of compositions that may be used for the manufacture of the primary lens and the secondary lens are as follows:
  the reference GF corresponds to a composition as described in WO 2006/063994, comprising a copolymer having 34% by weight of a hydrophilic methacrylic comonomer, such as HEMA; 58% by weight of a hydrophobic acrylic comonomer, such as EGPEA, and 8% by weight of a dimethacrylic comonomer, such as poly (propylene glycol) dimethacrylate.
  the reference HY26 corresponds to a Benzflex 26 intraocular lens material (Benz Research and Development, USA), comprising the HEMA monomer for the most part in its composition.

The primary and secondary lenses were machined in these different materials, and then hydrated in 0.9% NaCl saline. The inner surface of the secondary lens was then superficially dewatered by means of a flow of air for about ten seconds before being pressed onto the primary lens. The assembly was then steam sterilized at 121° C. for 30 min.

TABLE 1

| Sample number | Primary lens material | Secondary lens material | Thickness of secondary lens [mm] | MTF of primary lens, 24 h after peeling [100 m/mm, aperture 3 mm] |
|---|---|---|---|---|
| 1 | GF | HY26% | 0.2 | 0.55 |
| 2 | HY26% | GF | 0.2 | 0.57 |
| 3 | GF | GF | 0.2 | 0.56 |
| 4 | GF | HY26% | 0.1 | 0.56 |
| 5 | GF | GF | 0.1 | 0.55 |
| 6 | HY26% | HY26% | 0.1 | 0.36 |

Figure 5:
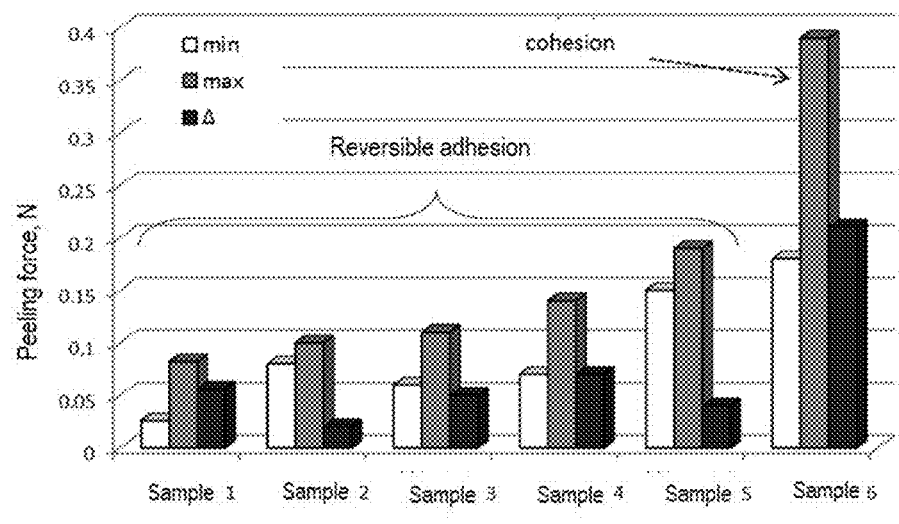
FIG. 5 shows the evolution of the peeling force for different compositions of materials of the primary and secondary lenses tested in the examples. The corresponding samples are described in Table 1.

The various combinations of primary lenses/secondary lenses tested are shown in Table 1. The primary lens is a diopter lens between 20 and 20.5 D. The force required for peeling is shown in FIG. 5. The peeling forces were measured using a traction/compression bench (FL Plus, Lloyd). The peeling rate was 50 mm/min. The primary lens was fixed on the low side and the secondary lens on the high side by clipping them between the jaws of two clamps. The peeling was effected in the air with hydrated lenses.

Figure 3:
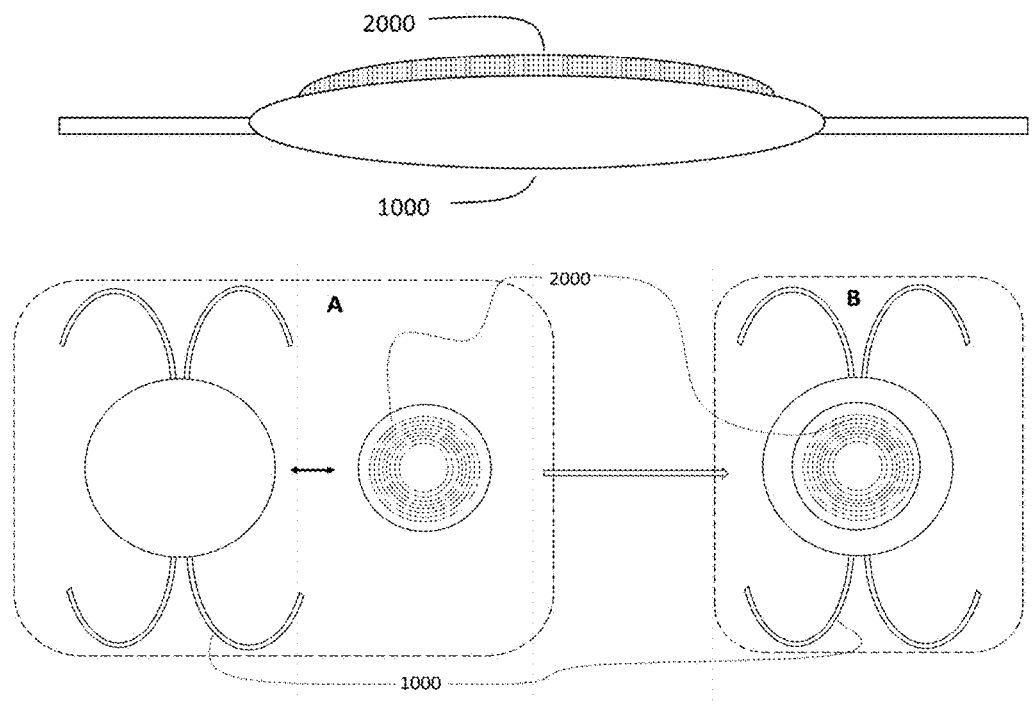
FIG. 3 shows another example of a lens according to the invention before (3-A) and after assembly (3-B).
Figure 4:
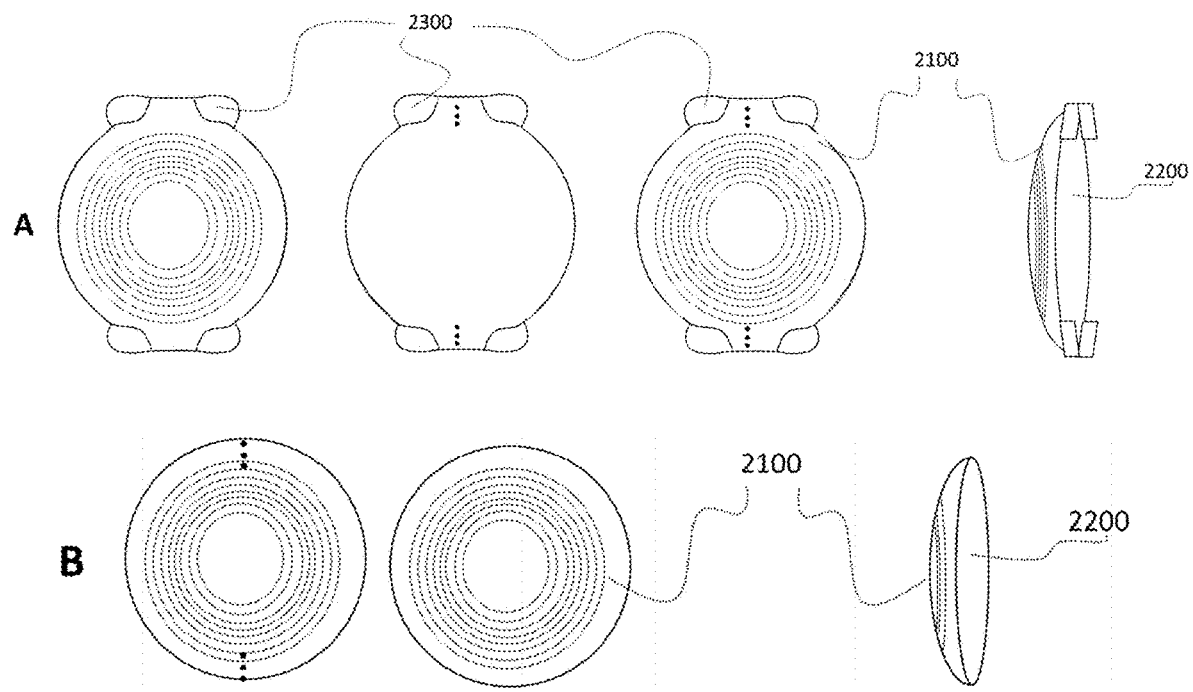
FIG. 4 shows examples of secondary lenses compatible with the corresponding conventional models of FIG. 1. The 4-A configuration is compatible with explantation within 6 months following implantation of the assembly. The 4-B configuration is compatible with explantation at any time following implantation.

FIG. 3 shows the peeling forces necessary to remove the secondary lens, and that the thinner the secondary lens, the higher is its adhesion. It also appears that the adhesion increases when the primary lens is of the same composition as the secondary lens. These two parameters, as well as, in the case of adhesion obtained by hydration, the degree of hydration, make it possible to easily modulate the degree of adhesion in order to obtain an adequate compromise between the stability of the implant and the ease of withdrawal. of the secondary lens.

Table 1 also shows the modulation transfer function (MTF) 24 hours after the removal of the secondary lens. This transfer function is a measure of the optical quality of the lens. Its value before assembly of the secondary lens is about 0.55 on the primary lenses tested.

It was observed, in the case of the sample 6, that excessive adhesion induces a partially cohesive failure accompanied by degradation of the optical properties of the primary lens. The optical qualities of the other primary lenses remained remarkably stable. In view of these results, it appears that peeling strengths between 0.025 and 0.2 N are adequate for the present invention.

Example 2

One advantage of the invention is to allow insertion of the two lenses of the IOL. To do this, the two lenses are assembled according to the procedures described above. In the present example, the compatibility of these assembled implants with the standard implantation procedures was tested. A model injector (Accuject 2.2-1p, Medicel, Switzerland) and a cohesive viscoelastic gel (Physiovisc Integral, Physiol, Belgium) were used. After injection of a sufficient amount of the gel into the cartridge, both preassembled primary and secondary lenses were loaded into a cartridge by a standard procedure known to those skilled in the art. Then, the assembly of the lenses was injected with a traction/compression bench (LF Plus, Lloyd) by a controlled movement of the piston with an injection speed of 100 mm/min.

Figure 6:
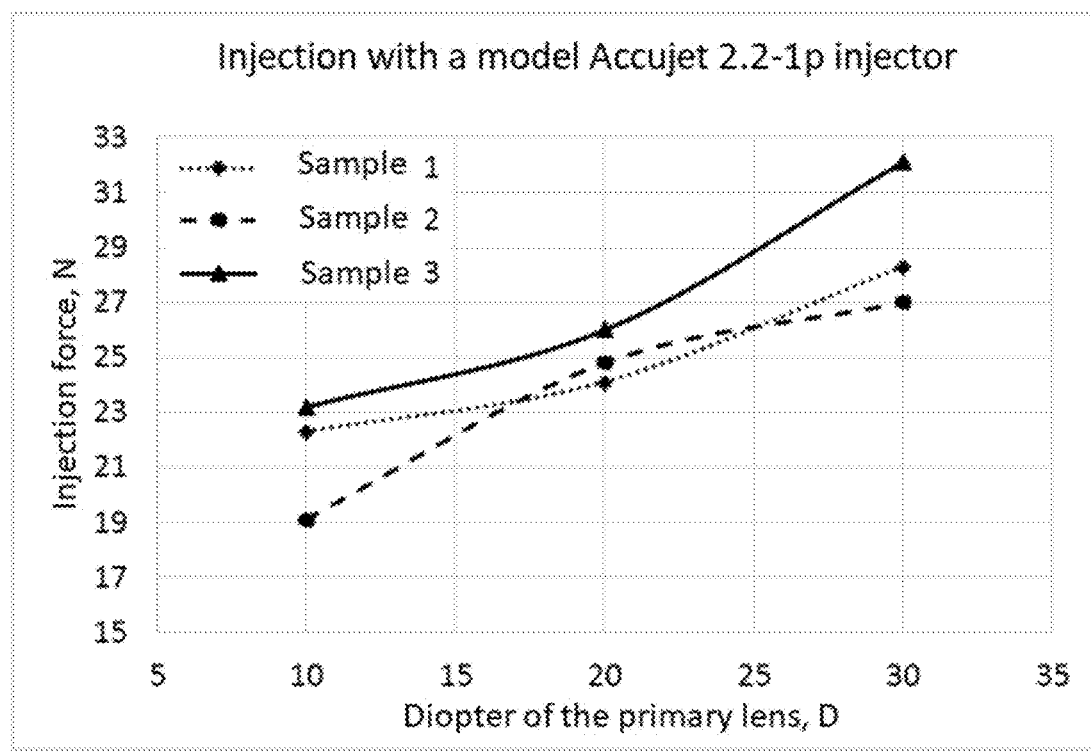
FIG. 6 shows the forces necessary for inserting the intraocular lenses of the examples.

Samples 1 to 3 of Table 1 were tested. The results of the injection forces are shown in FIG. 6. The measured forces are close to those measured for simple implants (primary lens only) and no misalignment or disassembly was observed after injection.

The invention claimed is:

1. An intraocular lens surgically implantable in the capsular bag, sulcus, or in the anterior chamber of the eye, the intraocular lens comprising:
  a primary lens having a first focal length, a first surface, and a second surface, the primary lens having one or more haptic portions for positioning the primary lens in the eye during implantation; and
  a secondary lens having a first surface and a second surface, wherein the second surface of the secondary lens conforms to the first surface of the primary lens, while the secondary lens is attached to the primary lens by peelable adhesive forces allowing peeling of the lenses by adhesive rupture on the second surface of the secondary lens, wherein a chemical composition of the primary lens and a chemical composition of the secondary lens are effective to result in a reversible interfacial interaction between the second surface of the secondary lens and the first surface of the primary lens, which includes an optical portion of the primary lens, and allowing removal of the secondary lens while the primary lens remains implanted in the eye without degrading the optical characteristics of the optical portion of the primary lens.

2. The intraocular lens according to claim 1 wherein the secondary lens has at least two focal lengths.

3. The intraocular lens according to claim 1, wherein the secondary lens has a diameter smaller than the diameter of an optical portion of the primary lens.

4. The intraocular lens according to claim 1, wherein the secondary lens has a diameter less than or equal to 5.00 mm.

5. The intraocular lens according to claim 1, wherein the secondary lens has a diameter smaller than the diameter of a rhexis of a capsular bag.

6. The intraocular lens according to claim 1, wherein the primary lens is a refractive lens.

7. The intraocular lens according to claim 6, wherein the refractive lens provides a clear view over a long distance.

8. The intraocular lens according to claim 7, wherein the refractive lens allows correction of corneal astigmatism.

9. The intraocular lens according to claim 1, wherein the secondary lens is a diffractive lens having an order x with an infinite focal length and at least one order x+1 having a finite focal length.

10. The intraocular lens according to claim 1, wherein the secondary lens is in the form of a thin meniscus having a central thickness of less than 500 μm.

11. The intraocular lens according to claim 10, wherein the thin meniscus has a central thickness of less than 200 μm.

12. The intraocular lens according to claim 1, wherein the combination of the primary lens and the secondary lens forms a multifocal lens whose optical characteristics make it possible to obtain a sharp image at great distances superimposed on a sharp image at short distance.

13. The intraocular lens according to claim 12, wherein the combination of the primary lens and the secondary lens further provides an additional focal distance that makes it possible to obtain a net image at intermediate distance.

14. The intraocular lens according to claim 1, wherein materials forming the primary lens and the secondary lens exhibit intrinsic adhesion that is sufficient to maintain the integrity of the primary lens and the secondary lens in an aqueous medium.

15. The intraocular lens according to claim 1, wherein materials forming the primary lens and the secondary lens comprise at least one copolymer, wherein the copolymer comprised in the primary lens comprises a monomer common with the copolymer comprised in the secondary lens.

16. The intraocular lens according to claim 15, wherein the common monomer is an acrylate.

17. The intraocular lens of claim 16, wherein the acrylate comprises one or more of 2-hydroxyethylmethylacrylate, methylmethacrylate, ethylmethylacrylate, hydroxyhexylmethacrylate, ethoxyethylmethacrylate, 2-phenylethylacrylate, ethylacrylate; 2-phenylethylmethacrylate, 2,2,2-trifluoroethylmethacrylate, ethylene-glycolphenyletheracrylate, butylacrylate, dimethyldiphenylsiloxane, dimethylsiloxane, and combinations thereof.

18. The intraocular lens according to claim 1, comprising centering means of the secondary lens on the primary lens.

19. The intraocular lens according to claim 18, wherein the centering means comprise an open recess in the primary lens to accommodate the secondary lens.

20. The intraocular lens according to claim 19, wherein the recess has a height equal to the height of the secondary lens.

* * * * *